US012336884B2

(12) United States Patent
Magidson et al.

(10) Patent No.: US 12,336,884 B2
(45) Date of Patent: Jun. 24, 2025

(54) FOAM EARPLUG WITH TRANSDERMAL MATERIAL

(71) Applicant: MOLDEX-METRIC, INC., Culver City, CA (US)

(72) Inventors: Mark Magidson, Los Angeles, CA (US); James Hornstein, Studio City, CA (US); Fred Ryan, Venice, CA (US)

(73) Assignee: Moldex-Metric, Inc., Culver City, CA (US)

( * ) Notice: Subject to any disclaimer, the term of this patent is extended or adjusted under 35 U.S.C. 154(b) by 459 days.

(21) Appl. No.: 17/480,116

(22) Filed: Sep. 20, 2021

(65) Prior Publication Data

US 2022/0087868 A1     Mar. 24, 2022

Related U.S. Application Data

(63) Continuation of application No. 16/164,013, filed on Oct. 18, 2018, now abandoned.

(51) Int. Cl.
| | | |
|---|---|---|
| *A61F 11/08* | (2006.01) | |
| *A61F 11/12* | (2006.01) | |
| *A61L 31/16* | (2006.01) | |
| *A61M 31/00* | (2006.01) | |
| *A61M 35/00* | (2006.01) | |

(52) U.S. Cl.
CPC ........... *A61F 11/08* (2013.01); *A61M 31/002* (2013.01); *A61F 11/085* (2022.01); *A61F 11/12* (2013.01); *A61L 31/16* (2013.01); *A61M 35/00* (2013.01); *A61M 2210/0662* (2013.01)

(58) Field of Classification Search
CPC ........ A61F 11/08; A61F 11/085; A61F 11/10; A61F 11/12
See application file for complete search history.

(56) References Cited

U.S. PATENT DOCUMENTS

| 4,774,938 A | 10/1988 | Leight |
| 4,869,339 A | 9/1989 | Barton |

(Continued)

OTHER PUBLICATIONS

"U.S. Appl. No. 18/520,400, Preliminary Amendment Filed Nov. 27, 2023", 9 pgs.

(Continued)

*Primary Examiner* — James M Mellott
(74) *Attorney, Agent, or Firm* — Schwegman Lundberg & Woessner, P.A.

(57) ABSTRACT

A foam earplug for reception at least partially within the ear canal and including a body portion formed of resilient foam plastic material having a multiple open cell structure and having a size and shape for at least partial reception within the ear canal. A transdermal material having a particular beneficial action, and with an outer layer of the foam earplug infused with the transdermal material so that the benefits of the transdermal material is in transdermal contact with the ear canal. One example is a humectant material and, specifically, a moisturizer/lubricating material, for providing an increase to the lubrication and moisturizing in the ear canal. A second example is where the beneficial action is provided by systemic distribution such as a sleep aid, i.e., Melatonin, so that when the earplugs are worn during sleep, the earplugs will provide a sleep aid to the wearer.

17 Claims, 2 Drawing Sheets

(56) References Cited

U.S. PATENT DOCUMENTS

| | | | |
|---|---|---|---|
| 5,264,219 | A | 11/1993 | Godbey et al. |
| 5,904,143 | A | 5/1999 | Magidson et al. |
| 5,954,682 | A | 9/1999 | Petrus |
| 12,082,994 | B2 | 9/2024 | Magidson et al. |
| 2004/0060567 | A1* | 4/2004 | Ligon, Sr. ............... A61F 11/08 128/864 |
| 2009/0214072 | A1 | 8/2009 | Staab et al. |
| 2011/0034575 | A1 | 2/2011 | Triouleyre et al. |
| 2014/0076336 | A1 | 3/2014 | Clayton et al. |
| 2015/0182382 | A1 | 7/2015 | Bobyrev |
| 2015/0359945 | A1* | 12/2015 | Rosenblatt ............... A61L 31/10 424/404 |
| 2017/0189348 | A1 | 7/2017 | Lee et al. |
| 2017/0305039 | A1 | 10/2017 | Schreiner |
| 2017/0305040 | A1 | 10/2017 | Schreiner et al. |
| 2020/0121507 | A1 | 4/2020 | Magidson et al. |
| 2024/0099890 | A1 | 3/2024 | Magidson et al. |
| 2024/0374431 | A1 | 11/2024 | Magidson et al. |
| 2024/0374432 | A1 | 11/2024 | Magidson et al. |
| 2025/0017783 | A1 | 1/2025 | Magidson et al. |

OTHER PUBLICATIONS

"U.S. Appl. No. 16/164,013, Restriction Requirement mailed Nov. 17, 2020", 6 pgs.

"U.S. Appl. No. 16/164,013, Response filed Jan. 8, 2021 to Restriction Requirement mailed Nov. 17, 2020", 3 pgs.

"U.S. Appl. No. 16/164,013, Non-Final Office Action mailed Mar. 30, 2021", 15 pgs.

Fluhr, J, "Glycerol—Just a Moisturizer? Biological and Biophysical Effects", In: Dry Skin and Moisturizers, CRC Press, (2005), 227-243.

"U.S. Appl. No. 18/520,400, Response filed May 14, 2024 to Non Final Office Action mailed Mar. 14, 2024", 8 pgs.

"U.S. Appl. No. 18/520,400, Notice of Allowance mailed Jun. 21, 2024", 12 pgs.

"U.S. Appl. No. 18/520,400, Restriction Requirement mailed Feb. 22, 2024", 6 pgs.

"U.S. Appl. No. 18/520,400, Response filed Feb. 27, 2024 to Restriction Requirement mailed Feb. 22, 2024", 5 pgs.

"U.S. Appl. No. 18/520,400, Non Final Office Action mailed Mar. 14, 2024", 7 pgs.

"U.S. Appl. No. 18/782,808, Preliminary Amendment filed Jul. 24, 2024", 5 pgs.

"U.S. Appl. No. 18/520,400, Corrected Notice of Allowability mailed Aug. 9, 2024", 2 pgs.

"U.S. Appl. No. 18/782,854, Non Final Office Action mailed Sep. 17, 2024", 17 pgs.

"U.S. Appl. No. 18/782,854, Final Office Action mailed Oct. 8, 2024", 20 pgs.

"U.S. Appl. No. 18/898,266, Response filed Feb. 4, 2025 to Non Final Office Action mailed Dec. 11, 2024", 8 pgs.

"U.S. Appl. No. 18/782,808, Notice of Allowance mailed Feb. 13, 2025", 7 pgs.

"U.S. Appl. No. 18/898,266, Notice of Allowance mailed Feb. 26, 2025", 9 pgs.

"U.S. Appl. No. 18/782,808, Corrected Notice of Allowability mailed Feb. 26, 2025", 6 pgs.

"U.S. Appl. No. 18/782,808, Restriction Requirement mailed Sep. 12, 2024", 6 pgs.

"U.S. Appl. No. 18/782,808, Response filed Sep. 26, 2024 to Restriction Requirement mailed Sep. 12, 2024", 5 pgs.

"U.S. Appl. No. 18/782,808, Non Final Office Action mailed Oct. 21, 2024", 11 pgs.

"U.S. Appl. No. 18/782,808, Response filed Dec. 3, 2024 to Non Final Office Action mailed Oct. 21, 2024", 8 pgs.

"U.S. Appl. No. 18/782,854, Response filed Dec. 3, 2024 to Non Final Office Action mailed Sep. 17, 2024", 12 pgs.

"U.S. Appl. No. 18/898,266, Non Final Office Action mailed Dec. 11, 2024", 10 pgs.

"U.S. Appl. No. 18/782,854, Response filed Mar. 19, 2025 to Final Office Action mailed Oct. 8, 2024", 11 pgs.

"U.S. Appl. No. 18/782,854, Notice of Allowance mailed Apr. 2, 2025", 12 pgs.

"U.S. Appl. No. 18/782,808, Examiner Interview Summary mailed Apr. 15, 2025", 2 pgs.

"U.S. Appl. No. 18/782,808, Notice of Allowance mailed Apr. 28, 2025", 8 pgs.

"U.S. Appl. No. 18/898,266, Corrected Notice of Allowability mailed May 2, 2025", 5 pgs.

"U.S. Appl. No. 18/898,266, Corrected Notice of Allowability mailed May 13, 2025", 5 pgs.

* cited by examiner

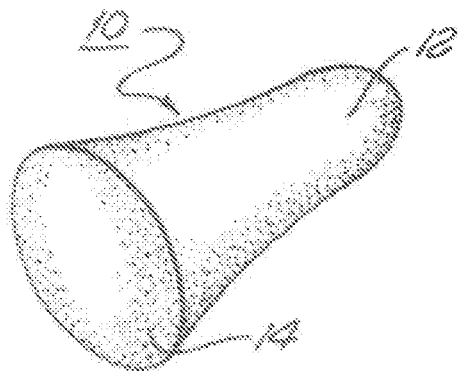
FIG. 1
PRIOR ART
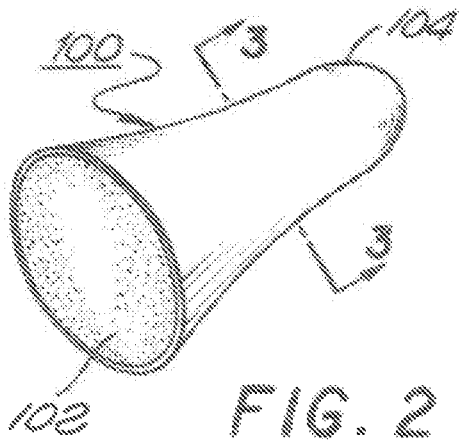
FIG. 2
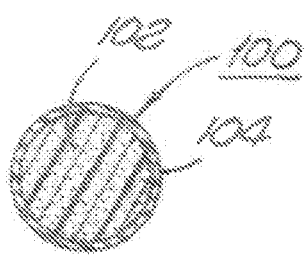
FIG. 3
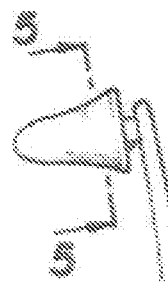
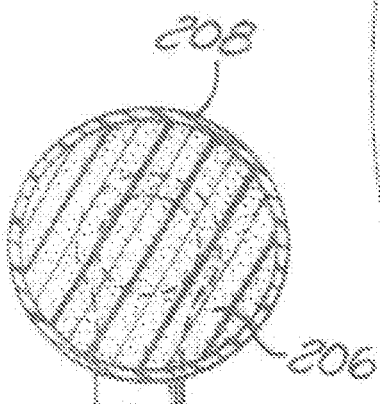
FIG. 5
FIG. 4

FOAM EARPLUG WITH TRANSDERMAL MATERIAL

This Continuation application is based on U.S. application Ser. No. 16/164,013 filed Oct. 18, 2018 by Mark Magidson, James Hornstein and Fred Ryan, Inventors, for Foam Earplugs with Transdermal Material.

BACKGROUND OF THE INVENTION

The present invention relates to a foam earplug and more specifically to a foam earplug that has an outer layer infused with a transdermal material such as a humectant material and specifically, a moisturizer/lubricating material. Also, the transdermal material may be a sleep aid such as Melatonin or a combination of the humectant and the sleep aid. In addition, the transdermal material can provide other beneficial effects so long as the active ingredient can be transferred to the body of the wearer by transdermal contact with the ear canal.

In the prior art, foam earplugs have been made of a slow recovery resilient foam material and such slow recovery earplugs have gained wide acceptance. As an example, an earplug as shown and described in U.S. Pat. No. RE29487 is used by rolling the earplug down to a small diameter and then inserting the rolled earplug into the ear. The earplug is then allowed to expand over a period of time, generally between a few seconds to as much as about a minute, to fill a substantial portion of the user's ear canal.

Foam earplugs, including slow recovery earplugs, may be made by a variety of techniques. One method of manufacturing is to punch out cylindrical earplugs from a sheet of foam material that has either a normal or slow recovery resiliency. A second method of manufacturing is to mold the earplug in a closed or open cavity mold to form the earplug in a desired shape. As an example, a molded earplug is shown in U.S. Pat. No. 4,774,938. This patent also demonstrates that a molded earplug will typically have smaller cells at the surface of the earplug since the molding process would tend to compress the cells at the surface. Whether the earplug is formed by cutting out of a sheet or by molding within a cavity, the outer surface is porous and allows the escape of air.

In the prior art there are times when it is difficult to insert earplugs properly into the ear canal when the ear canal is dry. Also, there are times when it is difficult to insert rolled down earplugs fully into the ear canal to obtain maximum attenuation in the ear canal if the surface of the ear canal resists insertion. In addition, when earplugs are located in the ear canal for long periods of time, the ear canal can become dry and itchy. This can occur, for example, when earplugs are worn during sleep or when used for hearing protection in industrial situations for long periods of time. It would therefore be advantageous to have an earplug, and, in particular a foam earplug, that is easier to insert and will ease dry and itchy ear canals after prolonged use. Also, when earplugs are worn during sleep, it would be beneficial if the earplug would provide a sleep aid to the wearer.

SUMMARY OF THE INVENTION

The present invention provides for a foam earplug for reception at least partially within the ear canal, including a body portion formed of resilient foam plastic material. The foam material has an open cell structure, a size and shape for at least partial reception within the ear canal. The earplug has an outer layer infused with a transdermal material. One example is a humectant material and specifically, a moisturizer/lubricating material, such that the outer layer is part of the body portion, at least in the area of the body portion received within the ear canal. This earplug structure provides an increase in the lubrication and moisturizing in the ear canal as compared to the resilient foam plastic material without the outer layer infused with the humectant material, Another example is to infuse the outer layer of the earplug with a sleep aid such as Melatonin so that when the earplugs are worn during sleep, the earplugs would provide a sleep aid to the wearer. In addition, the transdermal material can provide other beneficial effects so long as the active ingredient can be transferred to the body of the wearer by transdermal contact with the ear canal.

As a first method of making the earplugs of the present invention, a mold which has at least one, but normally a multitude of cavities, is provided for molding individual earplugs. Prior to the insertion of foamable plastic material, each cavity is coated with a coating of transdermal material. The foamable plastic material is then inserted into the coated transdermal material, the earplugs are removed and have the coating of transdermal material infused into the foamed earplug to form an outer layer of foam infused with the transdermal material. As indicated above, this structure provides a very beneficial result when the transdermal material is a humectant to provide an increase in the lubrication and moisturizing in the ear canal as compared to the resilient foam plastic material without the outer layer infused with the humectant material. When the transdermal material is Melatonin, the earplugs would provide a sleep aid to the wearer. In addition, the transdermal material can provide other beneficial effects so long as the active ingredient can be transferred to the body of the wearer by transdermal contact with the ear canal.

A second method of producing the earplug would be to mold the earplugs in the cavities or punch out from a sheet in the normal way. The individual earplugs then could be sprayed or dipped with a coating of transdermal material so that the transdermal material is infused into the foamed earplug to form an outer layer of foam infused with the transdermal material. The earplug itself may be made of different types of foam and with one embodiment using a slow recovery foam. In this way, the earplug can be rolled down for insertion into the ear and then as the slow recovery earplug recovers its original shape it fills the ear canal and the outer layer of foam infused with the transdermal material is now in contact with the surface of the ear canal. When using such a slow recovery foam, the outer layer of foam infused with the transdermal material normally would not cover the backend of the earplug so that air can escape out of an earplug when it is rolled down prior to insertion. Air can then re-enter into the earplug through the backend as the slow recovery foam recovers. Even if the backend of the earplug is infused with transdermal material, the foam earplug can be rolled down and then recover since the outer layer of foam infused with the transdermal material is still porous since the foam material is an open cell structure.

If the earplug is a push-in type that does not have to be rolled down prior to use, then the coating could cover the entire earplug including the backend. When the earplug has the entire earplug, including an outer layer of foam infused with the transdermal material including the backend of the earplug, the earplug will still be permeable to air. The outer layer of foam infused with the transdermal material is still porous since the outer layer of foam infused with the transdermal material is an open cell structure.

The humectant material could be made of a number of moisturizer/lubricating materials including moisturizer/lubricants using simple polyols and/or oils and other ingredients to provide the moisturizing/lubricating function. A specific example would be glycerin. Glycerin is water soluble and can be mixed with water in a ratio of one put glycerin to 2 parts water. Depending on the method of manufacturing, the mixture of glycerin and water can be sprayed or otherwise applied to the inside of an earplug cavity prior to molding the earplug or spraying an earplug after it is molded or punched out of a sheet of foam material. The humectant material will infiltrate the outer surface of the foam earplug since the foam material is hydrophilic and, for example, the glycerin and water mixture will be absorbed into the foam because of the water content of the mixture which in turn carries the glycerin into the foam and then forms the outer layer incorporating the glycerin. Either method of manufacture will produce an earplug having an outer layer of foam infused with the humectant material in a body portion of the earplug that will be in contact with the ear canal of a user.

Other examples of moisturizer/lubricating materials that may be used include a number of commercial products used in the hearing aid field that are used to aid in the insertion of hearing aids, molded to the exact size and shape of a user. In addition, some of these products aid in comfort due to the long use of the hearing aid in the ear canal. These products include those sold under the trade names and descriptions of the benefits of the products as follows:

"Otoferm™ Comfort Cream eases insertion and seals hearing aids. Silicon-based lubricant makes it easier to insert hearing aids and seals them for better sound."

"EARGENE® Ear Lotion Soothing, refreshing ear cream relieves and prevents itching and skin irritation resulting from extended wear of hearing aids."

"Ear Gel™ A soothing gel lubricant used to aid in the insertion of earmolds and hearing instruments."

"Audiologist's Choice® Anti-Itch Cream Hydrocortisone formula helps to relieve itchy ears with no sting, no pain. Maximum strength allowed without a prescription."

"Miracell® ProEar relieves itchy, irritated ear canals with nutritious ingredients that keep your ears healthy."

"Westone® Oto-Ease® makes wearing hearing aids easier and more comfortable. This unique formula provides a non-greasy, water-soluble solution for hearing device wearers while also helping create an effective acoustic seal."

All of the above products are specifically designed for use with hearing aids but are not incorporated in the structure of the hearing aid but am illustrative of moisturizer/lubricating materials that can be used in the ear canal and thereby serve as the humectant material in the present invention. If any of these prior art moisturizer/lubricating materials are not water soluble then most are soluble in alcohol or include alcohol as an ingredient. In either case, the alcohol mixture can be further mixed in water and that mixture can be used to produce the outer layer of foam material infused with the humectant material in the same manner as above.

As a further benefit of the ability to infuse the outer layer of the foam material with ingredients not initially soluble in water is to infuse the foam material with other ingredients that are beneficial to the user of the earplugs. Since one of the uses of the earplugs of the present invention is for use during sleep, the present invention also incorporates a sleep aid infused into the outer layer of the foam earplugs. In particular, Melatonin can be used either individually or in combination with the humectant material to provide a continuous supply of Melatonin during sleep. Reference is made to the following article:

"Use of Transdermal Melatonin Delivery to Improve Sleep Maintenance During Daytime" published in Clin Pharmacol Ther. 2009 October; 86(4); 378-382. The Abstract of this article indicates that "Oral melatonin can improve daytime sleep, but the hormone's short elimination half-life limits its use as a hypnotic in shift workers, jet-lag and other situations. Here we show in healthy subjects that transdermal delivery of melatonin during the daytime can elevate plasma melatonin and reduce waking after sleep onset by promoting sleep in the latter part of an 8-hour sleep opportunity. Thus, transdermal melatonin may have advantages over fast-release oral melatonin in improving sleep maintenance at adverse circadian phases".

Although the article is directed to daytime sleep for those who work a night shift and the earplugs of the present invention are useful for that purpose, the use of transdermal melatonin would also be beneficial for normal nighttime sleep. Melatonin, also known as N-acetyl-5-methoxy tryptamine, is a hormone that is produced by the pineal gland in humans and animals and regulates sleep and wakefulness. The compound is not soluble in water but is soluble in alcohol. As described above for other ingredients, the melatonin is first dissolved in alcohol and then in turn, the alcohol melatonin mixture is then further mixed with water to produce a final mixture to infuse into the foam earplug using the methods described above to form the outer layer of foam infused with melatonin to aid in sleep while wearing the earplugs.

It should also be appreciated that the foam earplug of the present invention may take a variety of forms including typically earplugs that are rolled or not rolled down and inserted into the car as well as semi-aural devices. These semi-aural devices are typically two ear protectors that are placed on opposite ends of a band which is constructed of plastic or metal. The band holds the ear protectors under tension partially within the ear canal, although not as deep as a typical earplug. Earplugs would normally have the highest noise reduction rating and the semi-aural headband devices would typically have a lower noise reduction rating. In either case, the use of the outer layer infused with the humectant material provides an increase in the lubrication and moisturizing in the ear canal as compared to the resilient foam plastic material without the outer layer infused with the humectant material or as a sleep aid if the outer layer is infused with Melatonin or a combination of both humectant material and Melatonin. In addition, when the transdermal material provides a beneficial effect and has at least one active ingredient that is transferred systemically to the body of the wearer by transdermal contact with the ear canal by the outer layer of foam infused with the at least one active ingredient this will provide the beneficial effect to the wearer of the earplug as compared to the resilient foam plastic material without outer layer of foam infused with the at least one active ingredient.

A clearer understanding of the invention will be had with reference to the following description and drawings.

BRIEF DESCRIPTION OF THE DRAWINGS

FIG. 1 is an illustration of a foam earplug of the prior art;
FIG. 2 is an illustration of a coated foam earplug in accordance with the present invention;
FIG. 3 is a cross-sectional view of the earplug taken along lines 3-3 in FIG. 2;

FIG. 4 is an illustration of a semi-aural headband type of earplug using ear protectors in accordance with the present invention;

FIG. 5 is a cross-sectional view of ear protectors taken along lines 5-5 of FIG. 4;

FIG. 1 illustrates a prior art earplug 10 typically molded from a slow recovery foam material. As can be seen, the earplug has a generally bullet-shape main body 12 with a flared outer end 14. This type of earplug would have the cells on the outer surface of the earplug typically being smaller at the outer surface and with larger cells in the center of the earplug. In this type of molded foam earplug since the surface of the earplug has smaller cells, a smoother configuration is generally formed on the outer cell surface than if the earplug were formed by cutting the earplug from a flat sheet. Although the earplug 10 may have smaller cells at the outer surface, the molded plugs are all porous on the outer surface although air may pass through the outer surface of the earplug a little more slowly than through the larger cells in the center of the plug.

Figure 6:
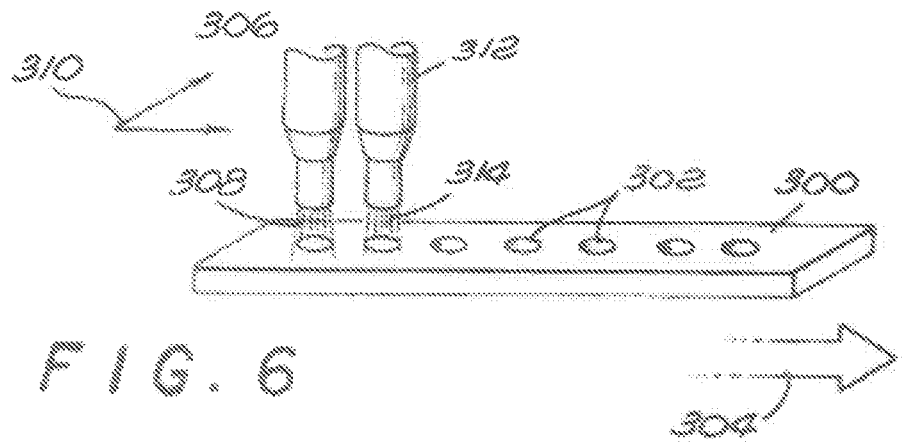
FIG. 6 is an illustration of a method of producing the earplug of the present invention including using coating inside the earplug mold cavity.

A first embodiment of the present invention is illustrated in FIGS. 2 and 3. The present invention has a plug 100 which has an inner body 102 and an outer layer 104 infused with a transdermal material. The earplug 100 has generally the same shape as the prior art earplug in having a bullet shape main body portion with a flared backend. The inner body 102 may be constructed of the slow recovery foam or other types of resilient foams and the outer layer infused with the transdermal material such as the humectant material or as a sleep aid if the outer layer is infused with melatonin or a combination of both. In addition, the transdermal material can provide other beneficial effects so long as the active ingredient can be transferred to the body of the wearer by transdermal contact with the ear canal.

As indicated above, the humectant material could be made of a number of moisturizer/lubricating materials and a specific example would be glycerin. Glycerin is water soluble and the glycerin can be mixed with water with a ratio of one part glycerin to 2 parts water. Other examples of moisturizer/lubricating materials that may be used include a number of commercial products used in the hearing aid field that will aid in the insertion of hearing aids, molded to the exact size and shape of a wearer. In addition, some of these products aid in comfort due to the long use of the hearing aid in the ear canal. These products are described above and are sold under the trade names and descriptions listed above.

The layer of foam 104 infused with the transdermal material as part of the foam earplug itself may generally have a thickness between 0.1 to 40 mils. A preferred thickness would typically be 0.1 to 20 mils. The foam material provides an excellent host for the transdermal material because of its open cell structure and can support sufficient storage of this transdermal material to supply the transdermal material to the ear canal for extended periods of time. The operation of the earplugs of the present invention is similar to the many products in common use referred to as transdermal patches that are applied to the skin to transmit various active ingredients to the body of the wearer through the skin. In addition, the present invention can provide other beneficial effects of prior art patches so long as the active ingredient of the transdermal material infused into the earplug can be transferred to the body of the wearer by transdermal contact with the ear canal.

By producing earplugs with the outer layer infused with the transdermal material such as the humectant material or as a sleep aid if the outer layer is infused with melatonin or a combination of both or any transdermal material that provides a beneficial effect with an active ingredient transferred to the body of the wearer by transdermal contact with the ear canal. As shown in FIGS. 2 and 3, it is believed that there is a synergistic effect between the benefits of the earplugs made of foam material, such as slow recovery foam material, and the benefits of the transdermal material infused into the outer layer of the foam earplug. Not only are the earplugs in direct contact with the skin in the ear canal to operate as a transdermal patch but in addition, the resiliency of the foam earplug maintains the earplug in constant contact with the ear canal and the supply of the transdermal material infused into the earplug to form the outer layer of the earplug is maintained by the outer layer of foam infused with transdermal material to a sufficient depth to supply the transdermal material to the ear canal for an extended period of time.

In addition to the form of the invention shown in FIGS. 2 and 3 it is also possible to have ear protectors, such as ear protectors 200, located at the ends of a headband 202 as shown in FIG. 4. This type of device provides for the ear protectors 200 to be partially inserted into the ear canal and to be held in the ear canal by the tension of the band 202. The band 202 may be constructed either of plastic or metal. As can be seen, the ear protectors 200 generally have a smaller insertable end 204 and a larger back portion 206 which typically would seal around the exterior of the opening to the ear canal.

FIG. 5 is a cross-sectional view of one of the ear protectors taken along lines 5-5 of FIG. 4 and, as can be seen, the ear protector is made of an interior foam material 206 with the outer layer 208 infused with the transdermal material such as the humectant material or as a sleep aid if the outer layer is infused with melatonin or a combination thereof. Again, the transdermal material may be any type of humectant material or sleep aid material or a combination of both. In addition, when the transdermal material provides a beneficial effect and has at least one active ingredient that is transferred systemically to the body of the wearer by transdermal contact with the ear canal by the outer layer of foam infused with the at least one active ingredient this will provide the beneficial effect to the wearer of the earplug as compared to the resilient foam plastic material without outer layer of foam infused with the at least one active ingredient.

The production of the earplug of the present invention may be produced by methods described with reference to FIGS. 6 to 8. In FIG. 6, a mold member 300 is shown to have multiple cavities 302, each having the form of an earplug or ear protector, shown in FIG. 2 or 4. Using the earplug shown in FIG. 2 as an example, the cavity would have a general bullet shape with a flared outer end. The cavity mold 300 is then moved as shown by the arrow 304 and with a first spray member 306 applying a pre-mold coating of the transdermal material 308 such as the humectant material or, if used as a sleep aid, the pre-mold coating is melatonin or a combination of both to the interior of each cavity 302. The spray head 306 may be actuated intermittently to ensure each cavity is coated with transdermal material 308 and without providing excess material to the exterior of the mold 300.

After each cavity 302 is coated with the transdermal material 308 an injector nozzle 312 fills each cavity with foamable plastic material 314 to form the main body of the earplug. After the foamable plastic material is completely foamed then the earplugs may be removed in the normal manner to produce the earplug as shown in FIG. 2. If it is desired to have the ends of earplugs also coated with the transdermal material, then the ends may be coated in a second step. This can be accomplished using the spray nozzle 306 before the earplugs are removed from the cavity or after the earplugs am removed from the cavities as shown in FIG. 8

Figure 7:
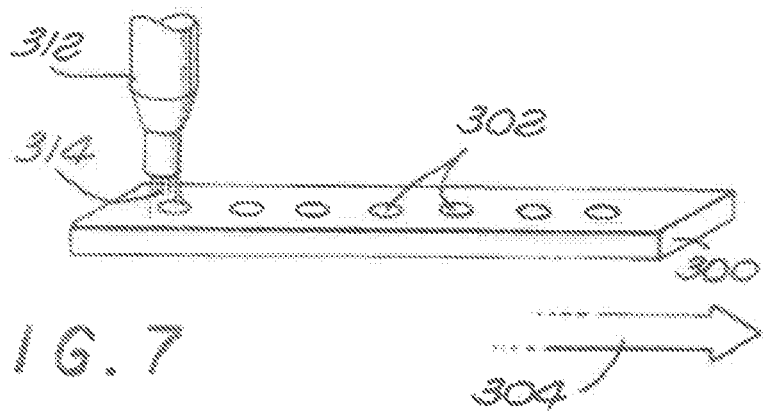
FIG. 7 is an illustration of a first step of a method of making an earplug of the present invention using a spray top-coat coating.
Figure 8:
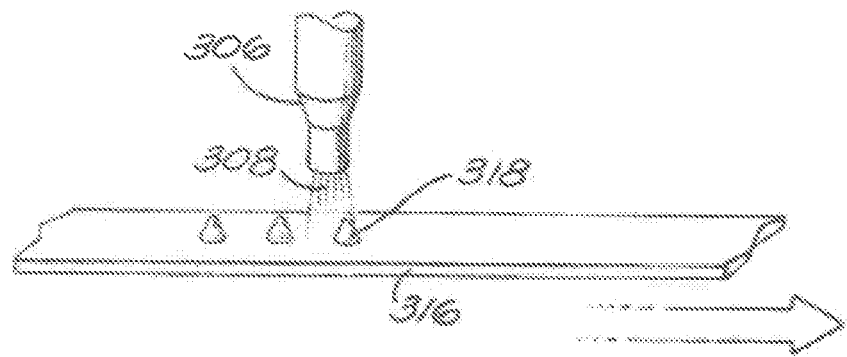
FIG. 8 is an illustration of a step of providing a spray top-coat coating which either completes the method of FIG. 7 or may provide an additional step for the method of FIG. 6.

In a second method of production shown in FIG. 7, the same cavity mold 300 having the plurality of cavities 302 is used and with the injection or nozzle 312 supplying foamable plastic material 314 to the interior of the cavities After the foamable plastic material has fully foamed, earplugs 318 are removed and may then be placed on a conveyer belt 316 shown in FIG. 8. The individual earplugs 318 are then sprayed using the sprayer head 306 with the transdermal material 308 to top coat the earplugs 318 with the coating.

The resultant earplug therefore has a body portion formed of resilient foam plastic material and an outer layer 104 or 209 foam infused with the transdermal material to form the layer integral with the body portion and with the combination having a synergistic effect between the benefits of the earplugs made of foam material, such as slow recovery foam material, and the benefits of the transdermal material infused into the foam to provide the outer layer.

Although the invention has been described with reference to particular embodiments, it is to be appreciated that various adaptations and modifications may be made. For example, the transdermal material can provide a variety of beneficial effects so long as the active ingredient can be transferred to the body of the wearer by transdermal contact with the ear canal. Therefore, the invention is only to be limited by the appended claims.

We claim:

1. A method of making a foam earplug having an outer layer infused with a transdermal material having a particular beneficial effect, including the following steps:
   providing a mold having at least one cavity of a size and shape corresponding to an earplug that fits at least partially within an ear canal;
   providing a foamable plastic material;
   injecting, via at least one nozzle, the foamable plastic material into the cavity;
   allowing the foamable plastic material to foam within the cavity to the size and shape of the cavity to form a resilient foam plastic earplug;
   removing the earplug from the cavity;
   providing the transdermal material having the particular beneficial effect; and
   coating the earplug with the transdermal material to form a resilient foam plastic earplug having an outer layer infused with the transdermal material,
   wherein the transdermal material comprises a sleep aid material.

2. The method of claim 1 wherein the foamable plastic material is provided to be a slow recovery foamable material, the slow recovery foamable material allowing the foam plastic earplug to be rolled down for insertion into an ear canal and, after insertion, recovers its original shape to fill the ear canal.

3. The method of claim 1 wherein the transdermal material infused in the outer layer further comprises a humectant material comprising a moisturizer/lubricating material.

4. The method of claim 3 wherein the humectant material is, specifically, glycerin.

5. The method of claim 1 wherein the sleep aid material comprises a Melatonin material.

6. The method of claim 1 wherein the transdermal material provides the beneficial effect and has at least one active ingredient that is transferred systemically to a body of a wearer by transdermal contact with the ear canal by the outer layer of foam infused with the at least one active ingredient to provide the beneficial effect to the wearer of the earplug as compared to the resilient foam plastic material without outer layer of foam infused with the at least one active ingredient.

7. The method of claim 1 wherein the cavity is provided with a size and shape to produce an earplug to be received substantially within exterior and interior portions of the ear canal.

8. The method of claim 1 wherein the cavity is provided with a size and shape to produce an earplug to be received only within an exterior portion of the ear canal.

9. The method of claim 1 wherein the outer layer is infused to a thickness in a range of 0.1 to 40 mils.

10. The method of claim 1 wherein the coating is applied by spraying.

11. The method of claim 1, wherein the coating the earplug with the transdermal material comprises:
    applying the transdermal material to an interior surface of the cavity prior to injecting the foamable plastic material into the cavity; and
    injecting, via the at least one nozzle, the foamable plastic material into the cavity, the transdermal material being coated on the earplug after the foamable plastic material is foamed within the cavity.

12. The method of claim 11, wherein the applying the transdermal material to an interior surface of the cavity comprises:
    actuating a spray head intermittently to ensure that the transdermal material is applied on the interior surface of the cavity without providing excess material to an exterior of the mold.

13. The method of claim 1, wherein the coating the earplug with the transdermal material comprises:
    applying the transdermal material on a surface of the earplug after removing the earplug from the cavity.

14. The method of claim 13, wherein the applying the transdermal material on the surface of the earplug after removing the earplug from the cavity comprises:
    placing the removed earplug on a conveyer belt with a flat surface of the earplug touching the conveyer belt; and
    spraying, via a spray head, the transdermal material on the surface of the earplug from a top of the earplug.

15. The method of claim 1, wherein the cavity has a conical shape with a flared outer end.

16. The method of claim 1, wherein the foamable plastic material forms smaller cells at an outer surface and larger cells in a center portion of the earplug.

17. The method of claim 1, further comprising:
    dissolving the transdermal material in alcohol; and
    mixing the transdermal material that is dissolved in alcohol with water to produce a mixture for coating.

* * * * *

UNITED STATES PATENT AND TRADEMARK OFFICE
CERTIFICATE OF CORRECTION

PATENT NO. : 12,336,884 B2
APPLICATION NO. : 17/480116
DATED : June 24, 2025
INVENTOR(S) : Magidson et al.

It is certified that error appears in the above-identified patent and that said Letters Patent is hereby corrected as shown below:

In the Specification

Column 1, Line 63, delete "car" and insert --ear-- therefor

Column 2, Line 7, delete "material," and insert --material.-- therefor

Column 2, Line 41, delete "carplug" and insert --earplug-- therefor

Column 2, Line 61, delete "carplug" and insert --earplug-- therefor

Column 3, Line 6, delete "put" and insert --part-- therefor

Column 4, Line 35, delete "car" and insert --ear-- therefor

Column 6, Line 26, delete "car" and insert --ear-- therefor

Column 7, Line 13, delete "am" and insert --are-- therefor

Column 7, Line 26, delete "209" and insert --208-- therefor

Signed and Sealed this
Tenth Day of February, 2026

John A. Squires
*Director of the United States Patent and Trademark Office*